US006720485B1

United States Patent
Schaffer et al.

(10) Patent No.: US 6,720,485 B1
(45) Date of Patent: Apr. 13, 2004

(54) CONTROLLING STARCH SYNTHESIS

(75) Inventors: Arthur Schaffer, Hashmonaim (IL); Ilan Levin, Mazkeret Batya (IL); Marina Petreikov, Rishon LeZion (IL); Moshe Bar, Rishon LeZion (IL)

(73) Assignee: State of Israel-Ministry of Agriculture, Beit Dagan (IS)

( * ) Notice: Subject to any disclaimer, the term of this patent is extended or adjusted under 35 U.S.C. 154(b) by 0 days.

(21) Appl. No.: 09/744,085

(22) PCT Filed: Jul. 19, 1999

(86) PCT No.: PCT/IL99/00396

§ 371 (c)(1), (2), (4) Date: Mar. 26, 2001

(87) PCT Pub. No.: WO00/05390

PCT Pub. Date: Feb. 3, 2000

(30) Foreign Application Priority Data

Jul. 20, 1998 (IL) .................................................. 125425

(51) Int. Cl.$^7$ ............................ A01H 1/06; A01H 5/00; A01H 5/08; A01H 5/10; C12N 9/12

(52) U.S. Cl. .................... 800/317.4; 800/263; 800/267; 800/269; 435/194

(58) Field of Search ................................ 800/263, 267, 800/269, 317.4; 435/194

(56) References Cited

U.S. PATENT DOCUMENTS

| | | | |
|---|---|---|---|
| 5,498,830 A | 3/1996 | Barry et al. ................. | 800/205 |
| 5,608,149 A | 3/1997 | Barry et al. ................. | 800/205 |
| 5,608,150 A | 3/1997 | Conner ....................... | 800/205 |
| 5,817,913 A | 10/1998 | Schaffer ...................... | 800/200 |

FOREIGN PATENT DOCUMENTS

| | | |
|---|---|---|
| WO | WO 91/19806 | 12/1991 |
| WO | WO 92/14831 | 9/1992 |
| WO | WO 94/22289 | 10/1994 |
| WO | WO 96/24679 | 8/1996 |

OTHER PUBLICATIONS

Van Ooijen et al. Theor. Appl. Genet. 89: 1007–1013, 1994.*
Azanza F et al., "Genes from *Lycopersicon chemielewskii* Affecting Tomato Quality During Fruit Ripening", Theoretical and Applied Genetics 1995, vol. 91, No. 3, Aug. 1995, pp. 495–504.
Dinar M et al., "The Relationship Between Starch Accumulation and Soluble Solids Content of Tomato *Lycopersicon–esclentum* Fruits", Journal of the American Society for Horticultural Science, 1981. vol. 106, No. 4, pp. 415–418.
Stark David M et al., "Improvement of Food Quality Traits Through Enhancement of Starch Biosynthesis", Conference, Lexington, Kentucky, USA, Oct. 1–4, 1995. vol. 792, pp. 26–36.

Schaffer Arthur A et al., "Sucrose—to–Starch Metabolism in Tomato Fruit Undergoing Transient Starch Accumulation", Plant Physiology, 1997, vol. 113, No. 3, pp. 739–746.
Schaffer Arthur A et al., "Modification of Carbohydrate Content in Developing Tomato Fruit", 94$^{th}$ Annual Int. Conf. of the American Society for Horticultural Science, Salt Lake City, Utah, USA, Jul. 23–26, 1997, vol. 32 No. 7, p. 551.
Miron D et al., "Sucrose Phosphate Synthase Sucrose Synthase and Invertase Activities in Developing Fruit of *Lycopersicon–esculentum* Mill. And the Sucrose Accumulating *Lycopersicon–hirsutum* Humb. And Bonpl", Plant Physiology (Bethesda) 1991, vol. 95, No. 2, pp. 623–627.
Park S W et al., "Molecular Cloning and Organ–Specific Expression of Three Isoforms of Tomato ADP–Glucose Pyrophosphorylase Gene", Gene: An International Journal of Genes and Genomes, GB, Elsevier Science Publishers, Barking, vol. 206, No. 2 Jan. 1998, 215–221.
Hadas R et al., "PCR–generated molecular markers for the invertase gene and sucrose accumulation in tomato", Theoretical and Applied Genetics, vol. 90 No. 7–8, 1995, pp. 1142–1148.
Schaffer Arthur A et al., "ADPglucose pyrophosphorylase activity and starch accumulation in immature tomato fruit: the effect of a *lycopersicon hirsutum*–derived introgression encoding for the large subunit", Plant Science (Shannon), Mar. 2000, vol. 152, No. 2, pp. 135–144.
Schaffer Arthur a et al., "Modification of carbohydrate content in developing tomato fruit", Hortscience Oct. 1999, vol. 34, No. 6, pp. 1024–1027.
Y. Eshed et al., "Introgressions from *Lycopersicon pennellii* can improve the soluble–solids yield of tomato hybrids", Theor. Appl. Genet., 88:891–897, 1994.
Y. Eshed, et al., *Lycopersicon esculentum* lines containing small overlapping introgressions from *L. pennellii*, Theor. Appl. Gent, 83:1027–1034, 1992.
Michael J. Giroux, et al., "A single gene mutation that increases maize seed weight", Proc. Natl. Acad. Sci. USA, vol. 93, pp. 5824–5829, Jun. 1996.
Preiss J et al., "Starch synthesis in sinks and sources" Marcel Dekker Publ. NYC, pp. 63–96, 1996, Photoassim. Distr. Plants Crops, Zamski et al, eds.
Y. Kanayama, et al., "Divergent fructokinase genes are differentially expressed in tomato", Plant Physiol. 1997, 113:1379–1384.
S. Yelle, et al., "Sink Metabolism in tomato fruit", Plant Physiol. 1991, vol. 95, p. 1026–1035.
Fei Wang, et al., "Isolation and sequencing of tomato fruit sucrose synthase cDNA", Plant Physiol. 1993, 103:1463–1464.

(List continued on next page.)

Primary Examiner—David T. Fox
(74) Attorney, Agent, or Firm—Ladas & Parry

(57) ABSTRACT

A method for controlling starch synthesis in tomatoes including providing a population of plants derived from interspecific crosses of Lycopersicon spp. with *Lycopersicon esculentum* genotypes, and selecting individuals of the population that each contain an allele of a gene that increases starch synthesis, the gene originating from the Lycopersicon spp.

9 Claims, 1 Drawing Sheet

OTHER PUBLICATIONS

H. Fu, et al., "Sink– and vascular–associated sucrose synthase functions are encoded by different gene classes in potato", The plant cell, vol. 7, 1369–1385, Sep. 1995.

J. D. Hewitt et al., "sink strength of fruits of two tomato genotypes differing in total fruit solids content", J. Amer. Soc. Hort. Soc. 107(5), 1982, pp. 896–900.

A.J. Walker, et al., "Carbon translocation in the tomato: carbon import and fruit growth", Ann. Bot. 41, 813–823, 1977.

C.M. Rick, "High soluble–solids content in large–fruited tomato lines derived from a wild green–fruited species", Hilgardia, 42:493–510, 1974.

Y. Kanayama, et al., "Tomato fructokinases exhibit differential expression and substrate regulation", Plant Physiol. 1998, 85–90, vol. 117.

Schaffer Arthur A et al., "Inhibition of fructokinase and sucrose synthase by cytosolic levels of fructose in young tomato fruit undergoing transient starch synthesis", Phys. Plant. 101:800–806, 1997.

Superscript Preamplification System, GibcoBRL Life Technologies, Gaithersburg, MD, USA, 1995.

S. Yelle, et al., "Sink metabolism in tomato fruit", Plant. Physiol. 1988, 87, 737–740.

Taq DNA Polymerase, Supernova DNA Polymers, Madi Ltd. Rishon Le–Zion, Israel, 1999.

Automater Thermocycler, MJ Research Ind. Watertown, Massachusetts, USA, 1998.

Chen B.Y. et al., "The electronic plant gene register", Plant Physiology, 109:1498, 1995.

pGEM–T and pGEM–T Easy Vector Systems, Promega Corp., Madison, WI, USA, 1997.

Trizol Reagent System, GibcoBRL Life Technologies, Gaithersburg, MD, USA, 1999.

\* cited by examiner

CONTROLLING STARCH SYNTHESIS

FIELD OF THE INVENTION

The present invention relates to a method of breeding tomatoes with increased starch content in the young fruit and subsequently increased soluble solids content in the mature fruit. In addition, it relates to the use of genes that increase starch in the tomato.

BACKGROUND OF THE INVENTION

The solids content of ripe tomato fruit is a major determinant of its quality. Increasing the soluble solids (largely sugars and organic acids) content and thereby improving the value of industry tomatoes and the taste of fresh market tomatoes have been the goal of research projects for many years. Several approaches to improving solids levels have been taken, encompassing both agrotechnical and genetic manipulations.

Soluble solids content of tomato fruit are primarily comprised of sugars, organic acids and salts. Collectively the soluble solids content is a major determinant of fruit quality, both for industry use and for fresh market consumption. Approximately half of the soluble solids content is contributed by the sugar fraction which, in all standard cultivars of *Lycopersicon esculentum*, consists of the monosaccharide reducing sugars glucose and fructose in approximately equimolar concentrations.

Several strategies to increase sugar concentration in ripe tomato fruit have been explored. Genetic manipulations include the transfer of undefined traits of high soluble solids from wild species of Lycopersicon (Rick C. M. 1974. Hilgardia 42:493–510; and Hewitt J. D., Dinar M. and Stevens M. A. 1982. J. Am. Soc. Hort Sci. 107:896–900) and more recently the transfer of the genetic trait of sucrose accumulation from the wild *Lycopersicon chmielewskii* (Yelle S., Hewitt J. D., Robinson N. L., Damon N. S. and Bennett A. B. 1988. Pl. Physiol. 87:737–740; and Yelle S., Chetelat R. T., Dorais M., Deverna J. W. and Bennett A. B. 1991. Pl. Physiol. 95:1026–1035.) and *L. hirsutum* (Miron D. and Schaffer A. A. 1991. Pl. Physiol. 95:623–627), as well as the transfer of the genetic trait of high fructose to glucose ratio in the mature fruit, from L hirsutum (U.S. patent application Ser. No. 08/530,216, the disclosure of which is incorporated herein by reference). The latter approach was made possible by the study of the components of carbohydrate metabolism in developing tomato fruit tissue with the purpose of identifying biochemical steps whose modification may lead to increased soluble carbohydrate content in the fruit (Yelle et al., 1988, 1991; Miron and Schaffer, 1991). Once identified, these biochemical processes could then be targeted for modification by classical genetic means, assisted by selection for the genotypic biochemical trait, or by molecular genetic strategies.

The young developing tomato fruit is characterized by a transient starch accumulation which can contribute over 25% of the dry weight of the fruit tissue. Starch concentration begins to increase within days after anthesis and reaches peak concentrations before the mature green stage (Schaffer, A. A. and Petteikov, M. 1997a. Plant Physiology 113:739–746). At the mature stage this starch is practically absent in the tomato fruit tissue. It has been hypothesized that the transiendy accumulated starch serves as a reservoir of carbohydrate for the later accumulation of soluble sugars in the mature fruit (Dinar M. and Stevens M. A. 1981. J. Am. Soc. Hort. Sci. 106:415418). Dinar and Stevens laid the groundwork for this hypothesis in their study comparing seven genotypes of tomato whose total soluble solids (TSS) values in the ripe fruit spanned the spectrum from 4.6 to 6.3 Brix. They found that TSS values in ripe fruit were positively correlated with starch content in young, immature fruit and proposed that the products of starch hydrolysis contribute to the accumulation of soluble sugars.

The tomato plant translocates photosynthate to the fruit in the form of sucrose (Walker L. J. and Ho L. C. 1977. Ann. Bot. 41:813–823) and therefore, the temporal accumulation of starch will presumably be determined by temporal changes in the activities of key enzymes involved in sucrose to starch metabolism. The enzymatic pathway of starch synthesis in young tomato fruit has been studied and described (Schaffer, A. A. and Petreikov, M. 1997a. Plant Physiology 113:739–746; Schaffer, A. A. and Petreikov, M. 1997b. Physiologia Plantarum 101:800–806). Four enzymes were identified Mat potentially limit starch accumulation in these fruit, based on their absolute activities, as well as on the developmental changes in their activities which correlate temporally with the developmental changes in starch levels. These enzymes include those that catalyze the initial steps of sucrose metabolism in the young fruit (sucrose synthase, E.C. 2.4.1.13, and fructokinase, E.C. 2.7.1.4) as well as the latter steps of starch synthesis (ADP-glucose pyrophosphorylase, E.C. 2.7.727, and starch synthase, E.C., 2.4.1.21). In addition, Schaffer and Petreikov have shown that starch accumulation is tissue specific, localized primarily in the columella and inner pericarp tissues, and suggested that relative contributions of these tissues to fruit bulk could impact on Suit starch content.

Research has clearly shown that one of the above mentioned enzymes, ADP-glucose pyrophosphorylase (ADPGPPase), may be limiting to starch synthesis in tomato fruit, as well as in other starch accumulating tissues, such as potato tubers. In Stark D. M., Barry G. F., and Kishore G. M. 1996. Ann. NY Cad Sci 792:26–36, transgenic tomato plants and potato plants were developed with a bacterial mutant form of ADPGPPase (*E. coli*, GlgC16, a glycogen overproducer). Transgenic tomatoes showed a higher starch content in the immature fruit and an increased sugar content in the mature fruit Transgenic potato tubers with the same bacterial gene construct also showed an increase in starch content. Reciprocally, inhibition of ADPGPPase activity decreased the starch content of transgenic potato tubers, further indicating the importance of ADPGPPase in controlling starch accumulation.

The use of a gene for ADPGPPase of bacterial origin requires molecular genetic manipulations in order for the gene to function in eucaryotic plant tissue. For example, it requires that an artificial gene construct be developed that will encode a fusion polypeptide containing a specific amino terminal Lot peptide, not present in the procaryotic gene, as well as other DNA sequence additions that will cause in plant cells transcriptional termination, and the addition of polyadenylated nucleotides to the 3' end of the RNA sequence. In comparison, the use of a plant gene for similar transformations does not require these manipulations. In addition, the development of plants with increased or modified activity of these enzymes, based on the natural transfer through classical breeding techniques of naturally occurring alleles of these genes, can benefit from a number of advantages. For example, classical breeding techniques lead to the positioning of the desired allele in the natural position of the gene of interest, leading to genetic stability and obviating the unpredictable "position" effects characteristic of the development of transgenic organisms. In addition, with respect to consumer preferences, there are obvious advantages of a naturally derived commercial product such as a tomato fruit, compared to a transgenically derived tomato fruit.

With resect to fructokinase, two genes from tomato fruit have been identified, cloned and sequenced (Kanayama, Y. et al. 1997. Plant Physiology 113:1379–13S4). One of these genes, FK2, is particularly involved in the metabolic pathway associated with starch synthesis (Kanayama et al. 1998. Plant Physiology 117:85–90). Similarly, the gene for sucrose synthase from tomato fruit has been cloned and sequenced (Wang, F., et at. Plant Physiology 103:1463–1464; ) and has been shown to be the gene for sucrose synthase of sink tissue (Fu, H. and Park, W. D. Plant Cell 7:1369–1385).

With respect to ADPGPPase, the enzyme functions in higher plants as a heterotetramer, comprised of two large and two small subunits (Preiss, J. and Sivak, M. In: Photoassimilate Distribution in Plants and Crops, Zamski, E. and Schaffer, A. A., eds., Marcel Dekker Publ, NYC, pp.63–96, 1996) which are under independent genetic control. Three separate *L. esculentum* genes coding for the large subunits and one gene for the small subunit have recently been cloned and sequenced (Chen, B. Y. and Janes, H., 1995, Plant Physiology 109.1498; Park, S. W. and Chung, W. I. 1998. Gene 206.215–221). Much effort has been made in order to identify sources of ADPGPPase genes in plants that may contribute to improving starch content, as for example in corn (Giroux, M. J. et al., Proc. Natl. Acad. Sci. USA 93:5824–5829), where site-specific mutation of the gene for the large subunit of ADPGPPase, using a transposable element Ds system, led to an insertion mutation of ADPGPPase which had decreased sensitivity to the ADPGPPase inhibitor, phosphate, as well as increased seed weight.

As regards to the use of wild species of Lycopersicon for the modification of carbohydrate metabolism in tomatoes, as described in U.S. patent application Ser. No. 08/530,216, although the fructose to glucose ratio in *L. hirsutum* is high, the actual amount of fructose and glucose is very low. Recombination of the genetic trait of fructose to glucose ratio, together with the trait of high glucose and fructose levels from *L. esculentum* yielded the unobvious and desirable trait of high levels of hexose, together with the high ratio of fructose to glucose. However, *L. hirsutum* fruit accumulate only low amounts of starch, as compared to the cultivated, *L. esculentum* (Miron and Schaffer, 1991, Plant Physiology 95:623–627). Similarly, other wild species of Lycopersicon also accumulate little starch (i.e., L chmielewskii, Yelle et at. 1988. Plant Physiology 87:737–740). Thus, the prior art has never expected or considered the use of wild tomatoes as a possible source of genetic variability for the increase in starch accumulation.

SUMMARY OF THE INVENTION

The present invention seeks to provide selection strategies for tomatoes with high starch content in the young fruit and subsequent high soluble solids in the mature fruit.

There is thus provided in accordance with a preferred embodiment of the present invention a method for controlling starch synthesis in tomatoes including providing a population of plants derived from interspecific crosses of Lycopersicon spp. with *Lycopersicon esculenum* genotypes, and selecting individuals of the population that each contain an allele of a gene that increases starch synthesis, the gene originating from the Lycopersicon spp.

In accordance with a preferred embodiment of the present invention the step of selecting includes selecting individuals that each contain the allele of the gene that encodes for an enzyme that catalyzes a metabolic step in starch synthesis.

Further in accordance with a preferred embodiment of the present invention the step of selecting includes selecting individuals that each contain the allele of the gene that encodes for a subunit of ADP-glucose pyrophosphorylase (ADPGPPase).

Still further in accordance with a preferred embodiment of the present invention the step of selecting includes selecting individuals that each contain the allele of the gene that encodes for a *Lycopersicon hirsutum*-derived subunit of ADPGPPase.

Additionally in accordance with a preferred embodiment of the present invention the step of selecting includes selecting by using a molecular marker for the gene.

In accordance with a preferred embodiment of the present invention the molecular marker is diagnostic for [includes step of selecting includes] a *Lycopersicon hirsutum*-derived large subunit (LS1) of ADPGPPase.

Further in accordance with a preferred embodiment of the present invention the step of selecting includes selecting by measuring activity of the enzyme in young fruit and selecting those young fruit with high activity of the enzyme.

Still further in accordance with a preferred embodiment of the present invention the step of selecting includes selecting by measuring ADPGPPase activity of the young fruit, and selecting those young fruit with high ADPGPPase activity.

In accordance with a preferred embodiment of the present invention the Lycopersicon spp. includes a Lycopersicon spp. of green-fruit Eriopersicon subgenus. Preferably the Lycopersicon spp. includes *Lycopersicon hirsutum*.

There is also provided in accordance with a preferred embodiment of the present invention a method of producing genetically transformed plants which have elevated starch content, including the steps of inserting into the genome of a plant cell a recombinant double stranded DNA molecule including a selected promoter, a structural DNA sequence that causes the production of an RNA sequence which encodes the above described ADPGPPase LS1 protein, obtaining transformed plant cells, and regenerating from the transformed plant cells genetically transformed plants with elevated starch content.

In accordance with a preferred embodiment of the present invention the plant cell is selected from the group consisting of a tomato cell, a potato cell, a cell from a solanaceous plant, a legume cell, and a grain crop cell.

Further in accordance with a preferred embodiment of the present invention the promoter is selected from the group consisting of an immature fruit promoter, a tuber promoter, and a seed promoter.

Still further in accordance with a preferred embodiment of the present invention the step of regenerating includes regenerating genetically transformed plants with elevated starch content in an immature fruit In accordance with a preferred embodiment of the present invention the step of regenerating includes regenerating genetically transformed plants with elevated starch content in a tuber.

Further in accordance with a preferred embodiment of the present invention the step of regenerating includes regenerating genetically transformed plants with elevated starch content in a seed.

Still further in accordance with a preferred embodiment of the present invention the methods of the present invention also include the step of propagating the individuals of the population or the genetically transformed plants. The propagating may be by vegetative propagation or by seed, for example.

There are also provided in accordance with a preferred embodiment of the present invention a plant produced according to any of the methods of the present invention, a fruit produced by such a plant, and a seed which when grown yields such a plant.

BRIEF DESCRIPTION OF THE DRAWINGS

The present invention will be understood and appreciated more fully from the following detailed description, taken in conjunction with the drawing in which.

Figure 1:
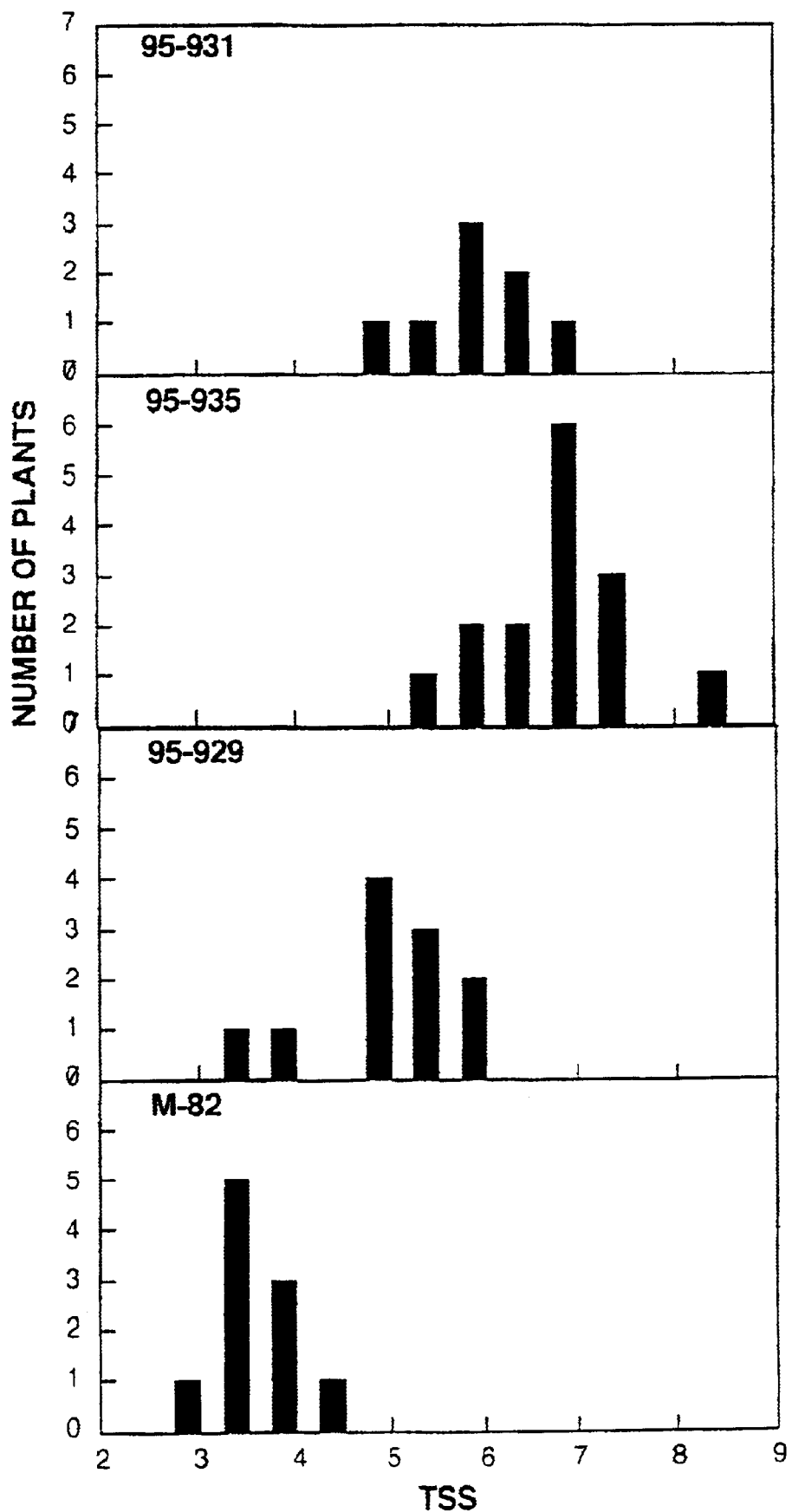
FIG. 1 is a histogram of TSS (total soluble solids) values from individual plants of three BCF6 lines (95–929, 95–931 and 95–935), compared to a standard cultivar, M-82. Data from each plant is an average of TSS values from 5 individual fruit. Single plant selections from 95–929, 95–931 and 95–935 led to the BCF7 high starch breeding lines 900, 901 and 904, respectively.

In addition, the following tables are presented:

Table 1 shows the starch levels and activity of enzymes involved in the metabolism of sucrose to starch in young tomato fruit of the breeding lines 900, 901 and 904, compared to the standard cultivar, M-82. The * signifies statistical difference between each individual high starch line when compared to M-82 and does not indicate differences between the high starch lines. For the enzymes PGI (phosphoglucosisomerase), PGM (phosphoglucomutase) and UDPGPPase only one fruit was analyzed per line and since enzyme activity in all lines was relatively high and apparently in excess (as in Schaffer and Peteikov, 1997a) no significant differences were assumed. For the other assays, a minimum of 4 fruit from individual plants were assayed.

Table 2 shows the TSS values of mature fruit, and the starch levels of immature fruit of M-82, 904, the hybrid between them, a mix of 11 hybrids between 904 and 11 introgression lines (described in text), and a mix of the 11 parallel hybrids between M-82 and the same 11 introgression lines. At least two fruit from each of the individual hybrids were measured and the average represents accordingly a minimum of 22 individual analyses. At least tree fruit from each of M-82, 904 and the hybrid between them were assayed.

Table 3 shows the enzyme activities of immature fruit pericarp of M-82, 904, the hybrid between them, a mix of 6 of the 11 hybrids between 904 and 11 introgression lines (described in text), and the parallel mix of 6 of the 11 hybrids between M-82 and the same introgression lines. For M-82, 904 and the hybrid between them, two fruit from individual plants were assayed.

Table 4 shows the nucleotide sequences of the forward and reverse primers used in the PCR analysis of the 3 large and 1 small subunits of ADPGPPase and the restriction endonucleases used to digest the PCR product in order to obtain the, L. hirsutum specific allele.

Table 5 shows the activity levels of ADPGPPase of F2 plants from the cross of line 904 and M-82. The LS1 genotype of the plants was characterized at the seedling stage, as described further herein. ADPGPPase activity and starch levels are the averages from 4 fruit (8–13 gr.) from individual F2 plants. TSS values are the average of a minimum of 5 fruit of each genotype.

Table 6 is the nucleotide sequence of [ADPGPPase LS1 (] ADPGlucose pyrophosphorylase, large subunit 1 (ADPGPPase LS1 from *L. hirsutum*.

Table 7 is the derived amino acid sequence for [ADPGPPase LS1 (] ADPGlucose pyrophosphorylase, large subunit 1 (ADPGPPase LS1) from *L. hirsutum*.

DETAILED DESCRIPTION OF A PREFERRED EMBODIMENT

The following is one example of carrying out the present invention. Plants of the *L. esculentum* breeding line 1630 (a Volcani Institute male sterile breeding line, used to simplify the production of the interspecific hybrid) were pollinated with pollen of the wild species *L. hirsutum* (LA1777). Hybrid F1 plants were grown and allowed to self pollinate, generating F2 seed. F2 seed were sown and about 350 plants were grown in a screenhouse and allowed to self pollinate.

Ripe fruit from each individual plant which produced fruit were individually analyzed for soluble solids (refractometrically). Only 25 of the interspecific F2 plants freely produced fruit. Pollen from one plant (F2-82) which was characterized by high soluble sugar level in the mature fruit (71 mg soluble sugar, composed of sucrose, glucose and fructose, per gram fresh weight of fruit) was used to pollinate a standard, industry type tomato (breeding line A701) for the production of the backcross-F1 (BC-F1) population. 100 BC-F1 plants were grown in the field and mature fruit of individual plants were analyzed for soluble solids, refractometrically, as well as soluble sugars, as above. A pedigree, single seed descent selection program was carried out, selecting the plants with highest total soluble solids and soluble sugar levels. Each generation consisted of at least 100 plants. This selection technique was carried out for six generations, until the BC-F7 generation, leading to breeding lines with higher solids levels than the standard industry type cultivars.

FIG. 1 shows a series of histograms representing the BCF6 lines from which three BCF7 breeding lines were selected. The BCF6 95–929 had an average TSS value of 4.8 (11 plants, 5 fruits per plant), the BCF6 95–931 had an average TSS value of 5.7 (8 plants, 5 fruits per plant) and the BCF6 95–935 had an average TSS value of 6.1 (15 plants, 5 fruits per plant), as compared to the standard cultivar, M-82 which had an average TSS value of 3.5 (10 plants, 5 fruits per plant). The individual plant selection 95–929-6, which led to the BCF7 line 900, had a TSS of 5.5 with a plant yield of 9.1 kg fruit The individual plant selection 95–931-2, which led to the BCF7 line 901, had a TSS of 6.5 with a plant yield of 7.2 kg fruit. The individual plant selection 95–935-5, which led to the BCF7 line 904, had a TSS of 6.6 with a plant yield of 4.7 kg fruit. The average plant yield of M-82 was 6.1 kg, based on an average of 6 plants.

In the BC-F7 generation immature fruit (approx. 15 days after anthesis) were measured for starch levels, as described in Schaffer and Petreikov (1997a). Lines 900, 901 and 904 were characterized by immature starch levels significantly higher than that of a standard industry type tomato cultivar, M-82 (Table 1). A comparative survey of enzymatic activities involved in sucrose to starch metabolism, as described in Schaffer and Petreikov (1997a), was performed on immature fruit of the two breeding lines and the standard, M-82. Typical results arc presented in Table 1 and show that breeding line 900 is characterized by significantly higher levels of activity of the enzymes ADPGPPase and fructokinase while lines 901 and 904 are characterized by significantly higher activities of the enzyme ADPGPPase alone. Line 904 is characterized by the highest levels of the enzyme ADPGPPase among the lines we studied and was used for further study of the role of ADPGPPase in starch accumulation and TSS levels of tomato fruit.

The high starch line 904 was further hybridized with eleven independent tomato breeding lines. In parallel, the standard industry type tomato cultivar, M-82, was similarly hybridized with each of these eleven lines. The eleven lines used were from the L. pennellii introgression lines (ILS). These introgression lines are a set of purebred lines each containing a small chromosome segment of the wild green-fruited Lycopersicon pennellii in the background of the cultivated L. esculentum cv M-82 (Eshed et al., 1992, Theor Appl. Genet., 83:1027–1034). These lines were developed from an initial interspecific cross between L. pennellii and L. esculentum cv M-82. The resulting F1 individuals were backcrossed to L. esculentum cv M-82 and selfed for several generations. During the process, chromosome segments of L. pennelli were selected for using restriction fragment length polymorphism probes covering the entire tomato genome. The introgression lines therefore provide a set of nearly-isogenic lines for segments of the wild-species genome and enable the association of yield traits with specific wild-species chromosome segments (Eshed Y. and Zamir D. 1994. Theor Appl. Genet., 88:891–897). Eleven such introgression lines were used for this study. The assumption was that crossing the 904 high starch line with this broad spectrum of genotypes, and crossing in parallel M-82 with the same identical genotypes would supply us with a broad spectrum of genetic background in which the genetic effect of 904 could be discerned.

Starch levels of the immature fruit, as well as soluble solids levels of the mature fruit, from the average of the eleven hybrids with line 904 were significantly higher than starch levels of immature fruit and soluble solids levels from mature fruit from the parallel hybrids with M82 (Table 2). A number of these immature fruit, representing the high starch hybrids with 904 and the low starch hybrids with M-82 were subjected to a detailed enzymatic analysis of the enzymes involved in sucrose to starch metabolism in the immature tomato fruit (as described above). Table 3 shows that of the ten enzymes assayed, only ADPGPPase activity was significantly higher in the hybrids with the high starch line (904), compared to the hybrids with the M-82 line.

TABLE 1

Starch levels and enzyme activities of immature tomato fruit (approximately 15 DAA) for CV M-82 and three high starch breeding lines 900, 901 and 904.

|  | M-82 | 900 | 901 | 904 |
| --- | --- | --- | --- | --- |
| Starch (mg/gfw) | 13.1 | 23.3* | 23.2* | 34.9* |
| Enzymes (mol/gfw//min) |  |  |  |  |
| Invertase | 15480 | 14690 | 18980 | 17870 |
| Sucrose synthase | 29570 | 31970 | 33260 | 27570 |
| fructokinase | 91 | 150* | 92 | 137 |
| phosphoglucomutase | 5760 | 6650 | 7830 | 7490 |
| phosphoglucosisomerase | 1950 | 2000 | 2870 | 2060 |
| UDPglu PPase | 15080 | 16760 | 17250 | 14760 |
| ADPglu PPase | 40 | 142* | 84* | 268* |

*Indicates statistical significance (P < 0.05) of each individual high starch line as compared to M-82.

TABLE 2

Starch content of immature fruit (approx. 15 days after anthesis) and °Brix (TSS) values of mature fruit of line 904, M-82, the hybrid between them, the mix of 11 hybrids between M-82 and 11 introgression lines (ILS) and the mix of 11 hybrids between 904 and the same 11 ILS.

| Genotype | Starch mg/gfw | °Brix |
| --- | --- | --- |
| M-82 | 23 b | 4.1 b |
| 904 | 58 a | 8.1 a |
| M-82 × 904 | 46 a | 7.1 a |
| M-82 × ILS | 25 b | 5.3 b |
| 904 × ILS | 44 a | 7.5 a |

Letters signify statistical significance at P < 0.05

TABLE 3

Activities of enzymes in the sucrose to starch metabolic pathway in immature tomato fruit.

|  | Activity (nmol/gfw/min) | | |
| --- | --- | --- | --- |
| Enzyme | 904 × ILS | M-82 × ILS | Ratio |
| Invertase | 520 | 620 | 0.83 |
| Sucrose synthase | 710 | 560 | 1.27 |
| fructokinase | 225 | 219 | 1.03 |
| glucokinase | 23 | 25 | 0.94 |
| phosphoglucomutase | 6900 | 5340 | 1.31 |
| phosphoglucoisomerase | 3160 | 2630 | 1.21 |
| UDPglu PPase | 8490 | 7130 | 1.19 |
| ADPglu PPase | 190 | 56 | 3.67* |
| starch synthase, sol. | 48 | 38 | 1.26 |
| starch synthase, insol. | 5 | 5 | 0.93 |

*statistical significance at P < 0.05

To further study the genetic trait for high ADPGPPase activity in immature fruit, specific DNA primers for the genes for the four ADPGPPase subunits (Chen and Janes, 1997 and Park and Cheung, 1998) were devised which could distinguish between the L. hirsutum derived gene and the L. esculentum derived gene, as described in the following paragraph.

PCR Analysis of ADPGPPase Subunits

Amplification reactions of the ADPGPPase subunits (25 µl final volume) contained 10 ng template DNA, 25 mM TAPS (pH=9.3 at 25° C.), 50 mM KCl, 2.5 mM $MgCl_2$, 1 M (mercaptoethanol, 0.2 mM of each of the four deoxyribonucleotide triphosphates (dATP, dCTP, dGTP and dTTP), 10 ng of each of the 2 primers (forward and reverse primers, see Table 4), and 1 unit of thermostable Taq DNA polymerase (SuperNova Taq polymerase, Madi Ltd., Rishon Le Zion, Israel). Reactions were carried out in an automated thermocycler (MJ Research Inc., Watertown, Mass., USA). Initial incubation was at 94° C. for 1 min, followed by 34 cycles of denaturation at 94° C. for 1 min, annealing at 55° C. for 1 min, and polymerization at 72° C. for 1 min and 45 sec. Final polymerization at 72° C. was carried out for 7 min after cycles were completed 10 µl of the amplification products were digested with 15 units of the restriction endonuclease found to generate the L. hirsutum specific alleles (Table 4). Digestions were carried out according to the manufacturer recommendations (New England Biolabs Inc., Beverly, Mass., USA). The digestion products were visualized by electrophoresis in 1.2% agarose gel and detected by staining with ethidum bromide.

Line 904 was shown to carry the L. hirsutum gene for large subunit 1 (LS1) while the other subunits of ADPGPPase in line 904 were shown to be derived from the L. esculentum.

In order to show that the L. hirsutum derived LS1 was correlated with increased ADPGPPase activity and increase starch level in the immature fruit, an F2 population of 64 plants of the cross between the high starch line 904 and the standard line M-82 was grown The plants were genotypically typed at the first true leaf stage to determine whether they were homozygous for the L. hirsutum ADPGPPase LS1 allele (HH), homozygous for the L. esculentum allele (EE) or heterozygous (HE) containing both alleles. The 64 F2 plants segregated for the LS1 in a ratio of 16:31:17, as expected for a single locus. Immature fruit from a minimum of 4 of each of the determined F2 genotypes were assayed for starch levels and for ADPGPPase activity. Results are presented in Table 5 and clearly show that the L. hirsutum allele for ADPGPPase LS1, as characterized by the specific PCR primers described, is associated with increased ADPGPPase activity in the immature fruit. Furthermore, the TSS values of the mature fruit was similarly influenced by the genotype of the LS1 gene.

TABLE 4

Forward and reverse primers used in the PCR analysis of the 3 large and 1 small subunits of ADPGPPase and the restriction endonuclease used to digest the PCR product in order to obtain the L. Hirsutum specific allele.

| ADPGPPase Subunit | Forward primer | Reverse primer | Restriction endonuclease |
|---|---|---|---|
| Large (LS1) | GTTCATTTGGGGA GAGTGAGCAC (Seq. ID No. 1) | GGGCAGCAGAAT TOTACTGTGTC (Seq. ID No. 2) | Hinf I |
| Large (LS2) | CTATTGGTGGTTG TTACCGGGT (Seq. ID No. 3) | CACTGTTCCAATA TCCTCCCAG (Seq. ID No. 4) | Hinf I |
| Large (LS3) | GCATATTGCTCGT GCGTACAAC (Seq. ID No. 5) | CTTTTCGCTGAG GACATGACC (Seq. ID No. 6) | — |
| Small | TTTCGTCTTCTCA TCTCGCCGGA (Seq. ID No. &) | GGCGATTTAGAG AGGCAGAGTTG (Seq. ID No. 8) | Rsal |

TABLE 5

Effect of genotype of LS1 on ADPGPPase activity and starch levels in immature fruit and TSS in mature fruit. ADPGPPase activity and starch levels are the averages from 4 fruit (8-13 gr.) from individual F2 plants. TSS values are the average of a minimum of 5 fruit of each genotype.

| Genotype | ADPGPPase | Starch | TSS |
|---|---|---|---|
| EE | 104 c | 16.4 b | 5.3 b |
| EH | 306 b | 25.2 ab | 5.9 ab |
| HH | 450 a | 37.3 a | 6.3 a |

Letters signify statistical difference at $P < 0.05$

Sequencing of the Gene Encoding ADPGPPase Large Subunit (LS1 from L. Hirsutum.

Total RNA was extracted from young fruits (3 grams in weight) of an individual plant homozygous for the ADPGPPase large subunit (LS1). The RNA extraction was carried out using the TRIzol reagent system (GibcoBRL life technologies, Gaithersburg, Md., USA). The total RNA was used as template for first strand cDNA synthesis using the Superscript preamplification system (GibcoBRL life technologies, Gaithersburg, Md., USA). The cDNA prepared was used as template in a PCR reaction to amplify the gene encoding ADPGPPase large subunit (LS). The DNA fragments containing the ADPGPPase large subunit (LS) were excised from an agarose gel and purified using the GENECLEAN II kit (BIO 101 inc., La Jolla Calif., USA). The PCR bands were then cloned into an pGEM-T Easy vector using the pGEM-T and PGEM-T Easy Vector Systems according to the manufacturer recommendations (Promega corporation, Madison, Wis., USA). The DNA clones were sequenced using an automated sequencer (Applied Biosystems, Foster City, Calif., USA).

Table 6 is the nucleotide sequence of ADPGPPase LS1 (ADPGlucose pyrophosphorylase, large subunit 1) from L. hirsutum (Seq. ID No. 9). Table 7 is the derived amino acid sequence for ADPGPPase LS1 (ADPGlucose pyrophosphorylase, large subunit 1) from L. hirsutum (Seq. ID No. 10).

TABLE 6

Nucleotide sequence of ADPGPPase LS1 (ADPGlucose pyrophosphorylase, large subunit 1) from L. hirsutum (Seq. ID. No. 9)

```
1     ATGAAATCGA CGGTTCATTT GGGGAGAGTG AGCACTGGTG GCTTTAACAA
51    TGGAGAGAAG GAGATTTTTG GGGAGAAGAT GAGAGGGAGT TTGAACAACA
101   ATCTCAGGAT TAATCAGTTG TCGAAAAGTT TGAAACTTGA GAAGAAGGAG
151   AAGAAGATTA AACCTOGGGT TGCTTACTCT GTGATCACTA CTGAAAATGA
201   CACAGAGACT GTGTTCGTAG ATATGCCACG TCTTGAGAGA COCCGGGCAA
251   ATCCCAAGGA TGTGGCTGCA GTCATATTAG GAGGAGGCGA AGGGACCAAG
301   TTATTCCCAC TTACAAGTAG AACTGCAACC CCTGCTGTTC CGGTTGGAGG
351   ATGCTACAGG CTCATAGACA TCCCGATGAG CAACTGTATC AACAGTGCTA
401   TTAACAAGAT TTTTGTGCTG ACACAGTACA ATTCTGCTGC CCTGAATCGT
451   CACATTGCTC GAACGTATTT TGGCAATGGT GTGAGCTTTG GAGATGGATT
501   TGTCGAGGTA CTAGCTGCAA CTCAGACACC TGGGGAAGCA GGAAAAAAAT
551   GGTTTCAAGG AACAGCAGAT GCTGTCAGAA AATTTATATG GGTTTTTGAG
601   GACGCTAAGA ACAAGAATAT TGAAAATATC CTTGTATTAT CTGGGGATCA
651   TCTTTATAGG ATGGATTATA TGGAGTTGGT GCAGAACCAT ATTGACAGAA
701   ATGCTGATAT TACTCTTTCA TGTGCACCAG CTGAGGACAG CCGAGCATCA
751   GATTTTGGGC TGGTCAAGAT TGACAGCAGA GGCAGAGTTG TCCAGTTTGC
801   TGAAAAACCA AAAGGTTTTG AGCTTAAAGC AATGCAAGTA GATACTACTC
851   TTGTTGGATT ATCTCCACAA GATGCGAAGA AATCCCCTTA TATTGCTTCA
901   ATGGGAGTTT ATGTTTTCAA GACAGATGTA TTGCTGAAGC TCTTGAAATG
951   GAGCTACCCC ACTTCTAATG ATTTTGGCTC TGAAATTATA CCAGCAGCTA
1001  TTGATGATTA CAATGTCCAA GCATACATTT TCAAAGACTA TTGGGAGGAC
1051  ATTGGAACAA TTAAATCTTT CTATAATGCT AGCTTGGCGC TCACACAAGA
```

TABLE 6-continued

Nucleotide sequence of ADPGPPase LS1 (ADPGlucose pyrophosphorylase, large subunit 1) from L. hirsutum (Seq. ID. No. 9)

```
1101    GTTTCCAGAG TTCCAATTTT ATGATCCAAA AACACCTTTT TACACATCTC
1151    CTAGGTTCCT TCCACCAACC AAGATAGACA ATTGCAAGAT TAAGGATGCC
1201    ATAATTTCTC ATGGATGTTT CTTGCGAGAT TGCTCTGTGG AACACTCCAT
1251    AGTGGGTGAA AGATCACGCT TAGACTGTGG TGTTGAACTG AAGGATACTT
1301    TCATGATGGG AGCAGACTAC TACCAAACAG AATCTGAGAT TGCCTCCCTG
1351    TTAGCAGAGG GGAAAGTACC GATTGGGATT GGGGAAAATA CAAAAATAAG
1401    GAAATGTATC ATTGACAAGA ACGCAAAGAT AGGAAAAAAT GTTTCAATCA
1451    TTAATAAAGA TGGTGTTCAA GAGGCAGACC GACCAGAGGA AGGATTCTAC
1501    ATACGATCAG GGATAACCAT TATATCAGAG AAAGCCACAA TTAGAGATGG
1551    AACAGTTATA TGA
```

TABLE 7

Derived amino acid sequence for ADPGPPase LS1 from L. hirsutum (Seq. ID No. 10).

MKSTVHLGRVSTGGFNNGEKEIFGEKMRGSLNNNLRINQL
SKSLKLEKKEKKIKPGVAYSVITTENDTETVFVDMPRLERRRAN
PKDVAAVILGGGEGTKLFPLTSRTATPAVPVGGCYRLIDIPMSNC
INSAINKIFVLTQYNSAALNRHIARTYFGNGVSFGDGFVEVLAAT
QTPGEAGKKWFQGTADAVRKFIWVFEDAKNKNIENILVLSGDHL
YRMDYMELVQNHIDRNADITLSCAPAEDSRASDFGLVKIDSRGR
VVQFAEKPKGFELKAMQVDTTLVGLSPQDAKKSPYIASMGVYV
FKTDVLLKLLKWSYPTSNDFGSEIIPAAIDDYNVQAYIFKDYWED
IGTIKSFYNASLALTQEFPEFQFYDPKTPFYTSPRFLPPTKIDNCKI
KDAIISHGCFLRDCSVEHSIVGERSRLDCGVELKDTFMMGADYY
QTESEIASLLAEGKVPIGIGENTKIRKCIIDKNAKIGKNVSIINKDG
VQEADRPEEGFYIRSGITIISEKATIRDGTVI

In the foregoing example, the large subunit 1 of ADPG-PPase was shown to increase starch level. Although not specifically tested, it is reasonable to assume that the present invention can also be carried out by transferring the *L. hirsutum* genes for any of the other 3 subunits of the enzyme, using the specific PCR markers developed for each of these genes, as they may also increase starch. In addition, transfer of ADPGPPase genes from other wild tomato species, other than *L. hirsutum*, may also increase starch in crosses with *L. esculentum*. Additionally, transfer of genes for other enzymes of starch synthesis from wild species, such as fructokinase and sucrose synthase for which the gene sequences from *L. esculentum* are known, may also increase starch levels.

Those skilled in the art will recognize that the described gene can be used to genetically transform plants to increase starch content. Plants that can genetically be transformed to have increased starch content include a large range of agriculturally important crops, such as but not limited to, potato, tomato, corn, wheat, cotton, banana, soybean, pea and rice. The plant transformation technology, including methods of transformation, such as the use of *Agrobacterium tumefaciens*, and methods of developing constructs, including the use of tissue specific promoters is well established and has recently been reviewed by Christou, P. ("Transformation technology", Trends in Plant Science, 1:423–431). There are presently available numerous promoters, including the constitutive promoters (CaMV) 35S and the maize ubiquitin promoter. In addition, there are, for example, organ/tissue specific promoters, for expression in seeds, tubers, immature fruit, mature fruit, pollen, roots and other organs.

The above examples are provided to better elucidate the practice of the present invention and should not be interpreted in any way to limit the scope of the present invention. Those skilled in the art will recognize that various modifications can be made to the methods described herein while not departing from the spirit and scope of the present invention.

What is claimed is:

1. A method for controlling starch synthesis in tomatoes comprising:

providing a population of plants derived from interspecific crosses a green-fruited wild species of the Lycopersicon genus (Lycopersicon spp.) with *Lycopersicon esculentum* genotypes; and selecting individuals of said population that each contain an allele of a gene that encodes for the large subunit (LS1) of ADP-zlucose pyrophosphorylase (ADPGPPase) and increases the activity of ADPGPPase, said allele originating from said Lycopersicon spp.

2. The method according to claim 1 wherein said step of selecting comprises selecting by using a molecular marker which is diagnostic for said allelgene.

3. The method according to claim 1 wherein said step of selecting comprises selecting by measuring ADPGPPase activity of said young fruit, and selecting those young fruit with high ADPGPPase activity.

4. A method according to claim 1 and additionally comprising the step of propagating said individuals of said population.

5. A method according to claim 4 wherein the step of propagating includes the step of vegetative propagation.

6. A method according to claim 4 wherein the step of propagating includes the of propagation by seed.

7. A plant produced according to the method of claim 1.

8. A fruit produced by the plant of claim 7.

9. A seed which when grown yields the plant of claim 7.

* * * * *

SEQUENCE LISTING

<160> NUMBER OF SEQ ID NOS: 10

<210> SEQ ID NO 1
<211> LENGTH: 23
<212> TYPE: DNA
<213> ORGANISM: Lycopersicon hirsutum

<400> SEQUENCE: 1
gttcatttgg ggagagtgag cac                                           23

<210> SEQ ID NO 2
<211> LENGTH: 23
<212> TYPE: DNA
<213> ORGANISM: Lycopersicon hirsutum

<400> SEQUENCE: 2
gggcagcaga attgtactgt gtc                                           23

-continued

```
<210> SEQ ID NO 3
<211> LENGTH: 22
<212> TYPE: DNA
<213> ORGANISM: Lycopersicon hirsutum

<400> SEQUENCE: 3
ctattggtgg ttgttaccgg gt                                              22

<210> SEQ ID NO 4
<211> LENGTH: 22
<212> TYPE: DNA
<213> ORGANISM: Lycopersicon hirsutum

<400> SEQUENCE: 4
cactgttcca atatcctccc ag                                              22

<210> SEQ ID NO 5
<211> LENGTH: 22
<212> TYPE: DNA
<213> ORGANISM: Lycopersicon hirsutum

<400> SEQUENCE: 5
gcatattgct cgtgcgtaca ac                                              22

<210> SEQ ID NO 6
<211> LENGTH: 22
<212> TYPE: DNA
<213> ORGANISM: Lycopersicon hirsutum

<400> SEQUENCE: 6
cttttcgctg aaggacatga cc                                              22

<210> SEQ ID NO 7
<211> LENGTH: 23
<212> TYPE: DNA
<213> ORGANISM: Lycopersicon hirsutum

<400> SEQUENCE: 7
tttcgtcttc tcatctcgcc gga                                             23

<210> SEQ ID NO 8
<211> LENGTH: 23
<212> TYPE: DNA
<213> ORGANISM: Lycopersicon hirsutum

<400> SEQUENCE: 8
ggcgatttag agaggcagag ttg                                             23

<210> SEQ ID NO 9
<211> LENGTH: 1563
<212> TYPE: DNA
<213> ORGANISM: Lycopersicon hirsutum
<220> FEATURE:
<221> NAME/KEY: CDS
<222> LOCATION: (1)..(1563)

<400> SEQUENCE: 9 atg aaa tcg acg gtt cat ttg ggg aga gtg agc act ggt ggc ttt aac     48
Met Lys Ser Thr Val His Leu Gly Arg Val Ser Thr Gly Gly Phe Asn
  1               5                  10                  15 aat gga gag aag gag att ttt ggg gag aag atg aga ggg agt ttg aac     96
Asn Gly Glu Lys Glu Ile Phe Gly Glu Lys Met Arg Gly Ser Leu Asn
             20                  25                  30 aac aat ctc agg att aat cag ttg tcg aaa agt ttg aaa ctt gag aag    144
```

-continued

```
                Asn Asn Leu Arg Ile Asn Gln Leu Ser Lys Ser Leu Lys Leu Glu Lys
                     35                  40                  45 aag gag aag aag att aaa cct ggg gtt gct tac tct gtg atc act act            192
Lys Glu Lys Lys Ile Lys Pro Gly Val Ala Tyr Ser Val Ile Thr Thr
 50                  55                  60 gaa aat gac aca gag act gtg ttc gta gat atg cca cgt ctt gag aga            240
Glu Asn Asp Thr Glu Thr Val Phe Val Asp Met Pro Arg Leu Glu Arg
 65                  70                  75                  80 cgc cgg gca aat ccc aag gat gtg gct gca gtc ata tta gga gga ggc            288
Arg Arg Ala Asn Pro Lys Asp Val Ala Ala Val Ile Leu Gly Gly Gly
                 85                  90                  95 gaa ggg acc aag tta ttc cca ctt aca agt aga act gca acc cct gct            336
Glu Gly Thr Lys Leu Phe Pro Leu Thr Ser Arg Thr Ala Thr Pro Ala
                100                 105                 110 gtt ccg gtt gga gga tgc tac agg ctc ata gac atc ccg atg agc aac            384
Val Pro Val Gly Gly Cys Tyr Arg Leu Ile Asp Ile Pro Met Ser Asn
                115                 120                 125 tgt atc aac agt gct att aac aag att ttt gtg ctg aca cag tac aat            432
Cys Ile Asn Ser Ala Ile Asn Lys Ile Phe Val Leu Thr Gln Tyr Asn
130                 135                 140 tct gct gcc ctg aat cgt cac att gct cga acg tat ttt ggc aat ggt            480
Ser Ala Ala Leu Asn Arg His Ile Ala Arg Thr Tyr Phe Gly Asn Gly
145                 150                 155                 160 gtg agc ttt gga gat gga ttt gtc gag gta cta gct gca act cag aca            528
Val Ser Phe Gly Asp Gly Phe Val Glu Val Leu Ala Ala Thr Gln Thr
                165                 170                 175 cct ggg gaa gca gga aaa aaa tgg ttt caa gga aca gca gat gct gtc            576
Pro Gly Glu Ala Gly Lys Lys Trp Phe Gln Gly Thr Ala Asp Ala Val
                180                 185                 190 aga aaa ttt ata tgg gtt ttt gag gac gct aag aac aag aat att gaa            624
Arg Lys Phe Ile Trp Val Phe Glu Asp Ala Lys Asn Lys Asn Ile Glu
                195                 200                 205 aat atc ctt gta tta tct ggg gat cat ctt tat agg atg gat tat atg            672
Asn Ile Leu Val Leu Ser Gly Asp His Leu Tyr Arg Met Asp Tyr Met
210                 215                 220 gag ttg gtg cag aac cat att gac aga aat gct gat att act ctt tca            720
Glu Leu Val Gln Asn His Ile Asp Arg Asn Ala Asp Ile Thr Leu Ser
225                 230                 235                 240 tgt gca cca gct gag gac agc cga gca tca gat ttt ggg ctg gtc aag            768
Cys Ala Pro Ala Glu Asp Ser Arg Ala Ser Asp Phe Gly Leu Val Lys
                245                 250                 255 att gac agc aga ggc aga gtt gtc cag ttt gct gaa aaa cca aaa ggt            816
Ile Asp Ser Arg Gly Arg Val Val Gln Phe Ala Glu Lys Pro Lys Gly
                260                 265                 270 ttt gag ctt aaa gca atg caa gta gat act act ctt gtt gga tta tct            864
Phe Glu Leu Lys Ala Met Gln Val Asp Thr Thr Leu Val Gly Leu Ser
                275                 280                 285 cca caa gat gcg aag aaa tcc cct tat att gct tca atg gga gtt tat            912
Pro Gln Asp Ala Lys Lys Ser Pro Tyr Ile Ala Ser Met Gly Val Tyr
                290                 295                 300 gtt ttc aag aca gat gta ttg ctg aag ctc ttg aaa tgg agc tac ccc            960
Val Phe Lys Thr Asp Val Leu Leu Lys Leu Leu Lys Trp Ser Tyr Pro
305                 310                 315                 320 act tct aat gat ttt ggc tct gaa att ata cca gca gct att gat gat           1008
Thr Ser Asn Asp Phe Gly Ser Glu Ile Ile Pro Ala Ala Ile Asp Asp
                325                 330                 335 tac aat gtc caa gca tac att ttc aaa gac tat tgg gag gac att gga           1056
Tyr Asn Val Gln Ala Tyr Ile Phe Lys Asp Tyr Trp Glu Asp Ile Gly
                340                 345                 350
```

```
aca att aaa tct ttc tat aat gct agc ttg gcg ctc aca caa gag ttt       1104
Thr Ile Lys Ser Phe Tyr Asn Ala Ser Leu Ala Leu Thr Gln Glu Phe
        355                 360                 365 cca gag ttc caa ttt tat gat cca aaa aca cct ttt tac aca tct cct       1152
Pro Glu Phe Gln Phe Tyr Asp Pro Lys Thr Pro Phe Tyr Thr Ser Pro
370                 375                 380 agg ttc ctt cca cca acc aag ata gac aat tgc aag att aag gat gcc       1200
Arg Phe Leu Pro Pro Thr Lys Ile Asp Asn Cys Lys Ile Lys Asp Ala
385                 390                 395                 400 ata att tct cat gga tgt ttc ttg cga gat tgc tct gtg gaa cac tcc       1248
Ile Ile Ser His Gly Cys Phe Leu Arg Asp Cys Ser Val Glu His Ser
            405                 410                 415 ata gtg ggt gaa aga tca cgc tta gac tgt ggt gtt gaa ctg aag gat       1296
Ile Val Gly Glu Arg Ser Arg Leu Asp Cys Gly Val Glu Leu Lys Asp
            420                 425                 430 act ttc atg atg gga gca gac tac tac caa aca gaa tct gag att gcc       1344
Thr Phe Met Met Gly Ala Asp Tyr Tyr Gln Thr Glu Ser Glu Ile Ala
        435                 440                 445 tcc ctg tta gca gag ggg aaa gta ccg att ggg att ggg gaa aat aca       1392
Ser Leu Leu Ala Glu Gly Lys Val Pro Ile Gly Ile Gly Glu Asn Thr
450                 455                 460 aaa ata agg aaa tgt atc att gac aag aac gca aag ata gga aaa aat       1440
Lys Ile Arg Lys Cys Ile Ile Asp Lys Asn Ala Lys Ile Gly Lys Asn
465                 470                 475                 480 gtt tca atc att aat aaa gat ggt gtt caa gag gca gac cga cca gag       1488
Val Ser Ile Ile Asn Lys Asp Gly Val Gln Glu Ala Asp Arg Pro Glu
            485                 490                 495 gaa gga ttc tac ata cga tca ggg ata acc att ata tca gag aaa gcc       1536
Glu Gly Phe Tyr Ile Arg Ser Gly Ile Thr Ile Ile Ser Glu Lys Ala
        500                 505                 510 aca att aga gat gga aca gtt ata tga                                    1563
Thr Ile Arg Asp Gly Thr Val Ile
            515                 520

<210> SEQ ID NO 10
<211> LENGTH: 520
<212> TYPE: PRT
<213> ORGANISM: Lycopersicon hirsutum

<400> SEQUENCE: 10

Met Lys Ser Thr Val His Leu Gly Arg Val Ser Thr Gly Gly Phe Asn
 1               5                  10                  15

Asn Gly Glu Lys Glu Ile Phe Gly Glu Lys Met Arg Gly Ser Leu Asn
            20                  25                  30

Asn Asn Leu Arg Ile Asn Gln Leu Ser Lys Ser Leu Lys Leu Glu Lys
        35                  40                  45

Lys Glu Lys Lys Ile Lys Pro Gly Val Ala Tyr Ser Val Ile Thr Thr
    50                  55                  60

Glu Asn Asp Thr Glu Thr Val Phe Val Asp Met Pro Arg Leu Glu Arg
65                  70                  75                  80

Arg Arg Ala Asn Pro Lys Asp Val Ala Ala Val Ile Leu Gly Gly Gly
                85                  90                  95

Glu Gly Thr Lys Leu Phe Pro Leu Thr Ser Arg Thr Ala Thr Pro Ala
            100                 105                 110

Val Pro Val Gly Gly Cys Tyr Arg Leu Ile Asp Ile Pro Met Ser Asn
        115                 120                 125

Cys Ile Asn Ser Ala Ile Asn Lys Ile Phe Val Leu Thr Gln Tyr Asn
    130                 135                 140
```

-continued

```
Ser Ala Ala Leu Asn Arg His Ile Ala Arg Thr Tyr Phe Gly Asn Gly
145                 150                 155                 160

Val Ser Phe Gly Asp Gly Phe Val Glu Val Leu Ala Ala Thr Gln Thr
            165                 170                 175

Pro Gly Glu Ala Gly Lys Lys Trp Phe Gln Gly Thr Ala Asp Ala Val
            180                 185                 190

Arg Lys Phe Ile Trp Val Phe Glu Asp Ala Lys Asn Lys Asn Ile Glu
            195                 200                 205

Asn Ile Leu Val Leu Ser Gly Asp His Leu Tyr Arg Met Asp Tyr Met
210                 215                 220

Glu Leu Val Gln Asn His Ile Asp Arg Asn Ala Asp Ile Thr Leu Ser
225                 230                 235                 240

Cys Ala Pro Ala Glu Asp Ser Arg Ala Ser Asp Phe Gly Leu Val Lys
            245                 250                 255

Ile Asp Ser Arg Gly Arg Val Val Gln Phe Ala Glu Lys Pro Lys Gly
            260                 265                 270

Phe Glu Leu Lys Ala Met Gln Val Asp Thr Thr Leu Val Gly Leu Ser
            275                 280                 285

Pro Gln Asp Ala Lys Lys Ser Pro Tyr Ile Ala Ser Met Gly Val Tyr
            290                 295                 300

Val Phe Lys Thr Asp Val Leu Leu Lys Leu Leu Lys Trp Ser Tyr Pro
305                 310                 315                 320

Thr Ser Asn Asp Phe Gly Ser Glu Ile Ile Pro Ala Ala Ile Asp Asp
            325                 330                 335

Tyr Asn Val Gln Ala Tyr Ile Phe Lys Asp Tyr Trp Glu Asp Ile Gly
            340                 345                 350

Thr Ile Lys Ser Phe Tyr Asn Ala Ser Leu Ala Leu Thr Gln Glu Phe
            355                 360                 365

Pro Glu Phe Gln Phe Tyr Asp Pro Lys Thr Pro Phe Tyr Thr Ser Pro
370                 375                 380

Arg Phe Leu Pro Pro Thr Lys Ile Asp Asn Cys Lys Ile Lys Asp Ala
385                 390                 395                 400

Ile Ile Ser His Gly Cys Phe Leu Arg Asp Cys Ser Val Glu His Ser
            405                 410                 415

Ile Val Gly Glu Arg Ser Arg Leu Asp Cys Gly Val Glu Leu Lys Asp
            420                 425                 430

Thr Phe Met Met Gly Ala Asp Tyr Tyr Gln Thr Glu Ser Glu Ile Ala
            435                 440                 445

Ser Leu Leu Ala Glu Gly Lys Val Pro Ile Gly Ile Gly Glu Asn Thr
450                 455                 460

Lys Ile Arg Lys Cys Ile Ile Asp Lys Asn Ala Lys Ile Gly Lys Asn
465                 470                 475                 480

Val Ser Ile Ile Asn Lys Asp Gly Val Gln Glu Ala Asp Arg Pro Glu
            485                 490                 495

Glu Gly Phe Tyr Ile Arg Ser Gly Ile Thr Ile Ile Ser Glu Lys Ala
            500                 505                 510

Thr Ile Arg Asp Gly Thr Val Ile
            515                 520
```